US011241186B2

United States Patent
Kaddan et al.

(10) Patent No.: US 11,241,186 B2
(45) Date of Patent: Feb. 8, 2022

(54) SYSTEMS AND METHODS FOR PROCESSING EEG SIGNALS OF A NEUROFEEDBACK PROTOCOL

(71) Applicant: Myndlift Ltd., Tel-Aviv (IL)

(72) Inventors: Aziz Kaddan, Tel-Aviv (IL); Anas Abu Mukh, Tel-Aviv (IL); Shiri Simon, Tel-Aviv (IL)

(73) Assignee: Myndlift Ltd., Tel-Aviv (IL)

( * ) Notice: Subject to any disclaimer, the term of this patent is extended or adjusted under 35 U.S.C. 154(b) by 761 days.

(21) Appl. No.: 15/860,705

(22) Filed: Jan. 3, 2018

(65) Prior Publication Data
US 2018/0184937 A1 Jul. 5, 2018

Related U.S. Application Data

(60) Provisional application No. 62/441,600, filed on Jan. 3, 2017.

(51) Int. Cl.
*A61B 5/375* (2021.01)
*A61B 5/00* (2006.01)
(Continued)

(52) U.S. Cl.
CPC .............. *A61B 5/375* (2021.01); *A61B 5/291* (2021.01); *A61B 5/374* (2021.01); *A61B 5/7267* (2013.01);
(Continued)

(58) Field of Classification Search
CPC ..... A61B 5/0482; A61B 5/048; A61B 5/7267; A61B 5/0478; A61B 5/168; A61B 5/486; A61B 5/7278; A61B 5/6814
See application file for complete search history.

(56) References Cited

U.S. PATENT DOCUMENTS

2006/0199159 A1* 9/2006 Ghiron ............... G09B 23/30
434/270
2008/0052333 A1* 2/2008 Ruiter ............... A61B 5/04021
708/8
(Continued)

OTHER PUBLICATIONS

Arns et al. "Efficacy of Neurofeedback Treatment in ADHD: The Effects on Inattention, Impulsivity and Hyperactivity: A Meta-Analysis", Clinical EEG and Neuroscience, 40(3): 180-189, Jul. 2009.
(Continued)

*Primary Examiner* — Jacqueline Cheng
*Assistant Examiner* — Tho Q Tran

(57) ABSTRACT

There is provided a method for simulating at least one wet electroencephalogram (EEG) signal from at least one dry EEG signals, comprising: receiving at least one dry EEG signal measured by dry EEG electrode(s) applied to locations on a head of a patient corresponding to at least one of temporal lobe or frontal lobe, computing at least one simulated wet EEG signal by applying a trained statistical model based on at least one dry EEG signal, the at least one simulated wet EEG signal simulating wet EEG signals measured by a wet EEG electrode applied to at least one location corresponding to at least one of: central, parietal lobe, and occipital lobe, and providing the at least one simulated wet EEG signal for adjusting feedback of a neurofeedback treatment applied by a neurofeedback device.

22 Claims, 6 Drawing Sheets

(51) Int. Cl.
   *A61B 5/291* (2021.01)
   *A61B 5/16* (2006.01)
   *A61B 5/374* (2021.01)
(52) U.S. Cl.
   CPC .............. *A61B 5/168* (2013.01); *A61B 5/486* (2013.01); *A61B 5/6814* (2013.01); *A61B 5/7278* (2013.01)

(56) References Cited

U.S. PATENT DOCUMENTS

2012/0046535 A1* 2/2012 Lin ..................... A61B 5/0408
   600/396
2019/0192033 A1* 6/2019 Nurflus ................ A61B 5/4064

OTHER PUBLICATIONS

Arns et al. "Evaluation of Neurofeedback in ADHD: The Long and Winding Road", Biological Psychiatry, 95: 108-115, Available Online Dec. 7, 2013.

Cortes et al. "Support-Vector Networks", Machine Learning, 20(3): 273-297, Sep. 1995.

Flisiak-Antonijczuk et al. "The Effects of EEG-Neurofeedback on ADHD Symptoms and EEG Parameters", European Psychiatry. Abstracts of the 21st European Congress of Psychiatry, 28(Suppl.1): # 1862, Jan. 2013.

Gevensleben et al. "Is Neurofeedback An Efficacious Treatment for ADHD? A Randomised Controlled Clinical Trial", The Journal of Child Psychology and Psychiatry, 50(7): 780-789, Jul. 2009.

Hammond "Neurofeedback With Anxiety and Affective Disorders", Child and Adolescent Psychiatric Clinics of North America. 14(1): 105-123, Jan. 31, 2005.

Lofthouse et al. "A Review of Neurofeedback Treatment for Pediatric ADHD", Journal of Attention Disorders, 16(5): 351-372, Jul. 2012.

Moriyama et al. "Evidence-Based Information on the Clinical Use of Neurofeedback for ADHD", Neurotherapeutics, 9(3): 588-598, Published Online Aug. 25, 2012.

Swets "Signal Detection Theory and ROC Analysis in Psychology and Diagnostics: Collected Papers," Lawrence Erlbaum Associates: Mahwah, NJ, 1996: 4 pages. Book Description.

Tan et al. "Meta-Analysis of EEG Biofeedback in Treating Epilepsy", Clinical EEG and Neuroscience, 40(3): 173-179, Jul. 2009.

Thomson "Spectrum Estimation and Harmonic Analysis", Proceedings of the IEEE, 70(9): 1055-1096, Sep. 1982.

* cited by examiner

SYSTEMS AND METHODS FOR PROCESSING EEG SIGNALS OF A NEUROFEEDBACK PROTOCOL

RELATED APPLICATION

This application claims the benefit of priority under 35 USC 119(e) of U.S. Provisional Patent Application No. 62/441,600 filed on Jan. 3, 2017, the contents of which are incorporated herein by reference in their entirety.

BACKGROUND OF THE INVENTION

The present invention, in some embodiments thereof, relates to neurofeedback and, more specifically, but not exclusively, to systems and methods for processing electroencephalogram (EEG) signals of a neurofeedback treatment.

Neurofeedback is used as a treatment of various neurological and psychiatric disorders, for example, attention deficit hyperactivity disorder (ADHD), depression, anxiety, and epilepsy. The goal of neurofeedback is to train the patient to normalize EEG measurements that are abnormal relative to the healthy population. During neurofeedback training, the brain activity is measured in real-time and used as feedback to the patient. The feedback is commonly provided using video or sound used as positive feedback when the desired brain activity is recorded. In addition or alternatively, negative feedback is delivered when the recorded brain activity is undesirable. Over several training sessions the patient increases his\her awareness of how a normalized EEG pattern "feels" and how to control it.

SUMMARY OF THE INVENTION

According to a first aspect, a method for simulating at least one wet electroencephalogram (EEG) signal from at least one dry EEG signals, comprises:
receiving at least one dry EEG signal measured by dry EEG electrode(s) applied to locations on a head of a patient corresponding to at least one of temporal lobe or frontal lobe; computing at least one simulated wet EEG signal by applying a trained statistical model based on at least one dry EEG signal, the at least one simulated wet EEG signal simulating wet EEG signals measured by a wet EEG electrode applied to at least one location corresponding to at least one of: central, parietal lobe, and occipital lobe; and providing the at least one simulated wet EEG signal for adjusting feedback of a neurofeedback treatment applied by a neurofeedback device.

The simulated wet EEG signal is an estimate (within a tolerance requirement) of the actual wet EEG signal that would otherwise be measured using an actual wet EEG electrode(s) applied to the head of the patient.

The simulated wet EEG signal may represent wet EEG signals as would be measured at a location on the head of the patient that is unsuitable for placement of a dry EEG electrode. The simulated wet EEG signals generate feedback for the patient during the neurofeedback treatment, without actual application of wet EEG electrodes, using the applied dry EEG electrodes. The simulated wet EEG signals may simulate signals that would otherwise be collected from a certain location on the head of the patient, without actually placing the wet EEG electrode at the certain location, using dry EEG signals collected from dry EEG electrodes positioned at other locations on the head of the patient.

The systems and/or methods (e.g., code instructions stored in a storage device executed by one or more processors) described herein provide a technical solution to the technical problem of improving accuracy of feedback provided during neurofeedback treatments based on dry EEG signals. A simulated wet EEG signal is computed based on one or more dry EEG signals measured by respective dry EEG electrodes applied to the head of the patient. The simulated wet EEG signal is computed using the trained model without actually applying the wet EEG electrode(s) to the patient.

The systems and/or methods (e.g., code instructions stored in a storage device executed by one or more processors) described herein improve performance by adding a new feature(s) to the computing unit that is used to apply neurofeedback treatment. The performance of the computing unit used to apply neurofeedback treatment is improved relative to existing units used to apply neurofeedback. For example, the statistical model described herein (that outputs the simulated wet EEG signal based on the inputted dry EEG signal) provide the ability to infer from dry EEG electrodes, optionally using existing processor(s) and/or available memory, the signal in the wet EEG electrode. The simulated wet EEG signal represents the brain signal of the patient in the location of the wet channel based on the dry EEG signals.

The simulated wet EEG signal estimate the signal in a specific location defined for a specific neurofeedback protocol. As described in additional detail herein, the neurofeedback protocol may be based on one or more of: the location of the wet EEG electrode, frequency bands of the treatment, the training of the user, the type of feedback, and the duration and frequency of treatment. Therefore, feedback provided to the patient based on the simulated wet EEG signal provides a more accurate and therapeutically superior feedback during the neurofeedback treatment in comparison to feedback provided based on dry EEG signals alone.

In a first possible implementation of the method according to the first aspect, the dry EEG electrodes are applied to locations on the head of the patient without hair, and the at least one simulated wet EEG signal simulates measurements performed at least at one location on the head of the patient with hair.

In a second possible implementation form of the method according to the first aspect as such or according to any of the preceding implementation forms of the first aspect, the locations of the at least one dry EEG electrode and at least one wet EEG electrode denoting the location of the at least one simulated wet EEG signal are non-overlapping.

In a third possible implementation form of the method according to the first aspect as such or according to any of the preceding implementation forms of the first aspect, the at least one dry EEG signal is received during application of the neurofeedback treatment without actually applying the wet EEG electrode.

In a fourth possible implementation form of the method according to the first aspect as such or according to any of the preceding implementation forms of the first aspect, the at least one simulated wet EEG signal denotes a location on the head of the patient unsuitable for placement of the dry EEG electrode.

In a fifth possible implementation form of the method according to the first aspect as such or according to any of the preceding implementation forms of the first aspect, the simulated wet EEG signal is an estimate of a wet EEG signals measured at one or more EEG channels selected from the group consisting of: C3, C4, Cz, P3, Pz, P4, O1, Oz, O2, and intermediate locations thereof.

In a sixth possible implementation form of the method according to the first aspect as such or according to any of the preceding implementation forms of the first aspect, the dry EEG signals are measured from EEG channels selected from the group consisting of: Fpz, Fp1, Fp2, F3, F4, Fz, F7, F8, T3, T4, Tp9, Tp10, and intermediate locations thereof.

In a seventh possible implementation form of the method according to the first aspect as such or according to any of the preceding implementation forms of the first aspect, the simulated wet EEG signals is an estimate of a wet EEG signal measured at the Cz EEG channel, and the dry EEG signals are measured from at least one member selected from the group consisting of: Tp9, Fp1, Fp2, AF7, AFB, and Tp10.

In an eighth possible implementation form of the method according to the first aspect as such or according to any of the preceding implementation forms of the first aspect, the method further comprises computing a classification label based on a classification threshold applied to the simulated wet EEG signal, the classification label used by a neurofeedback device to adjust at least one media item according to a neurofeedback protocol administered to the patient.

In a ninth possible implementation form of the method according to the first aspect as such or according to any of the preceding implementation forms of the first aspect, the location for placement of a wet EEG electrode corresponding to the at least one simulated wet EEG signal is determined according to a neurofeedback protocol administered to the patient, wherein the wet EEG electrode is not actually applied to the patient.

In a tenth possible implementation form of the method according to the first aspect as such or according to any of the preceding implementation forms of the first aspect, the trained statistical model maps a plurality of set of values of a feature space corresponding to at least one dry EEG channel to a classification label of the at least one simulated wet EEG channel at each time window, wherein the classification label is determined according to a predefined classification threshold indicative of positive or negative feedback to the neurofeedback treatment.

In an eleventh possible implementation form of the method according to the first aspect as such or according to any of the preceding implementation forms of the first aspect, the at least one simulated wet EEG signal estimates the corresponding actual wet EEG signal as would have been measured by the actual wet EEG electrode applied to the head using conductive gel.

In a twelfth possible implementation form of the method according to the first aspect as such or according to any of the preceding implementation forms of the first aspect, the at least one simulated wet EEG signal estimates the corresponding actual wet EEG signal measured by the actual wet EEG electrode having a location on the head of the patient having hair.

According to a second aspect, a method for training a statistical model for simulating at least one wet electroencephalogram (EEG) signal from at least one dry EEG signal, comprises: receiving at least one dry EEG signal measured by dry EEG electrodes applied to locations on a head of a patient corresponding to at least one of temporal lobe and frontal lobe; receiving at least one wet EEG signal measured by wet EEG electrodes applied to at least one location corresponding to at least one of: central, parietal lobe, and occipital lobe; wherein the at least one wet EEG and the at least one dry EEG signals are simultaneously received; computing a statistical model using the at least one dry EEG signal as input for the training data and the at least one wet EEG signal as output for the training data, the statistical model computed to simulate at least one wet EEG signal based on at least one dry EEG signal; and providing the statistical model for computing at least one simulated wet EEG signal based on at least one dry EEG signal measured using dry EEG signals.

In a first possible implementation of the method according to the second aspect, the at least one wet EEG signal and the at least one dry EEG signal are simultaneously received during an administered neurofeedback treatment.

In a second possible implementation form of the method according to the second aspect as such or according to any of the preceding implementation forms of the second aspect, the method further comprises computing at least one classification label based on a classification threshold, the classification label indicative of feedback for an administered neurofeedback treatment based on adjustment of at least one media item, wherein computing the statistical model comprises computing the statistical model using the at least one classification label as the output training data.

In a third possible implementation form of the method according to the second aspect as such or according to any of the preceding implementation forms of the second aspect, time windows assigned with positive labels are computed based on the at least one wet EEG signal above a classification threshold indicative of a rewarding setting of feedback adjustment according to the neurofeedback protocol, and other time windows including negative values computed based on the at least one wet EEG below the classification threshold indicative of a punishing setting of the feedback adjustment according to the neurofeedback protocol, and wherein the statistical model is computed to output the positive or negative classification label according to the at least one dry EEG signal.

In a fourth possible implementation form of the method according to the second aspect as such or according to any of the preceding implementation forms of the second aspect, the at least one simulated wet EEG signal is computed as a weighted combination of a plurality of dry EEG signals.

In a fifth possible implementation form of the method according to the second aspect as such or according to any of the preceding implementation forms of the second aspect, computing the statistical models comprise computing a plurality of statistical models based on a plurality of different classification or regression algorithms, each of the plurality of statistical models computed based on a first time interval portion of the at least one wet EEG and the at least one dry EEG signals, and selecting the statistical model from the plurality of statistical models according to a probability of accurate prediction within the tolerance requirement using the remaining time interval portion of the at least one wet EEG and the at least one dry EEG signals.

In a sixth possible implementation form of the method according to the second aspect as such or according to any of the preceding implementation forms of the second aspect, the computing of the statistical model further comprises computing a feature space using power measured at each of a plurality of frequency bands compute for each of the measured dry EEG signals over a current and potentially previous time windows.

In a seventh possible implementation form of the method according to the second aspect as such or according to any of the preceding implementation forms of the second aspect, the method further comprises processing the at least one wet EEG and the at least one dry EEG signal to identify a plurality of frequency bands, and training the statistical model to simulate the at least one wet EEG signal for each of the plurality of frequency bands, wherein the plurality of frequency bands are selected from the group consisting of: theta (4-7 hertz (Hz)), alpha1 (8-10 Hz), alpha2 (11-13 Hz), beta1 (12-15 Hz), and beta2 (16-25 Hz).

In an eighth possible implementation form of the method according to the second aspect as such or according to any of the preceding implementation forms of the second aspect, the statistical model is trained based on linear discriminant analysis (LDA) methods.

According to a third aspect, a method for application of a neurofeedback treatment based on a simulated wet electroencephalogram (EEG) signal computed from at least one dry EEG signal, comprises: receiving at least one dry EEG signal measured by dry EEG electrodes applied to locations on a head of a patient corresponding to at least one of temporal lobe and frontal lobe; applying a trained statistical model to the at least one dry EEG signal to compute a classification label indicative of at least one of positive feedback and negative feedback for a neurofeedback treatment being administered to a patient, the classification label represent an estimate of whether the signal is above or below classification threshold applied to at least one wet EEG signal measured by at least one wet EEG electrode at a location defined by the neurofeedback protocol corresponding to at least one of: central, parietal lobe, and occipital lobe; and adjusting at least one media item according to at least one of the positive feedback and negative feedback.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
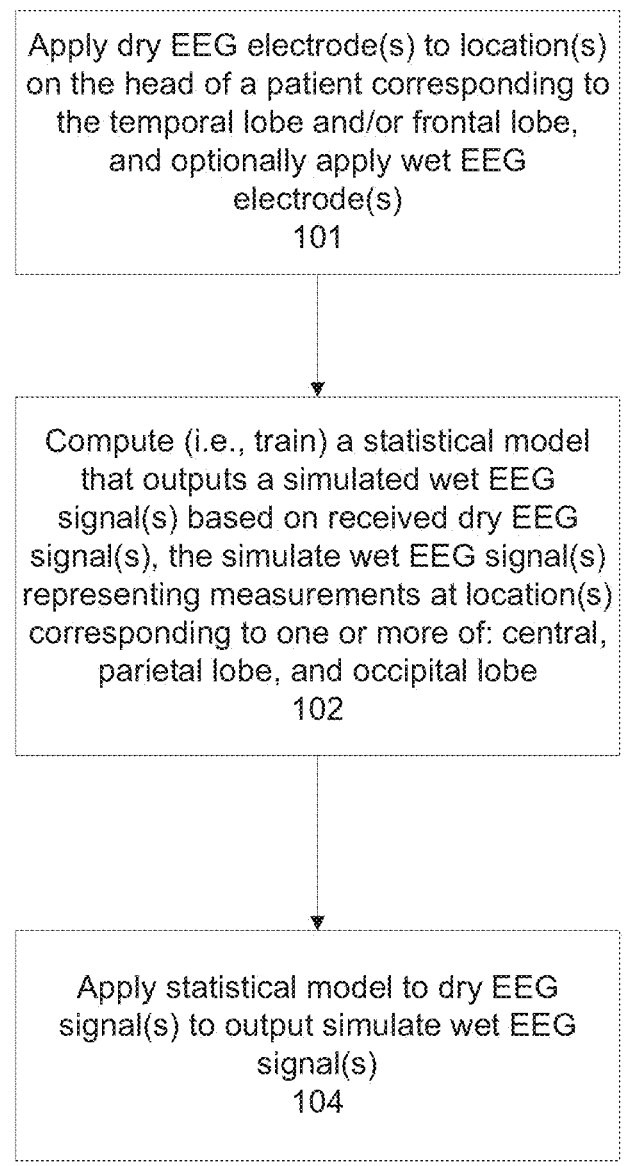
FIG. 1 is a flowchart of a method for training and/or using a statistical model that computes simulated wet EEG signals from measured dry EEG signals, in accordance with some embodiments of the present invention.

The present invention, in some embodiments thereof, relates to neurofeedback and, more specifically, but not exclusively, to systems and methods for processing electroencephalogram (EEG) signals of a neurofeedback treatment.

An aspect of some embodiments of the present invention relates to systems and/or methods (e.g., code instructions stored in a storage device executed by one or more processors) that compute a simulated wet EEG signal(s) (denoting EEG signals measured using conductive gel) from one or more dry EEG signals (measured without using conductive gel). The simulated wet EEG signal(s) is used to control feedback during a neurofeedback treatment, for example, to adjust image(s) and/or sound to provide positive or negative feedback. The dry EEG signals are obtained by dry EEG electrodes positioned on the head (e.g. scalp, forehead, temple) of the patient at locations corresponding to the temporal and/or frontal lobe, for example, at one or more of the following EEG channels based on the 10-20 standard: Fpz, Fp1, Fp2, Fz, Af7, Af8, Tp9, Tp10, and intermediate locations thereof. The dry EEG electrodes may be positioned at locations without hair.

The simulated wet EEG signals simulate EEG signals that would otherwise be obtained (i.e., when the neurofeedback treatment is administered using standard methods) by positioning wet EEG electrodes at locations corresponding to central, and/or parietal lobe, and/or occipital lobe. For example, at one or more of the following EEG channels based on the 10-20 standard: F3, F4, F7, F8, T3, T4, C3, C4, Cz, P3, Pz, P4, O1, Oz, O2, and intermediate locations thereof. The wet EEG electrodes may be positioned at locations that normally have growing hair. The dry EEG electrodes are placed in locations that are non-overlapping with locations of wet EEG electrodes as defined by the neurofeedback treatment.

The simulated wet EEG signal is an estimate (within a tolerance requirement) of the actual wet EEG signal that would otherwise be measured using an actual wet EEG electrode(s) applied to the head of the patient.

The simulated wet EEG signal may represent wet EEG signals as would be measured at a location on the head of the patient that is unsuitable for placement of a dry EEG electrode. The simulated wet EEG signals generate feedback for the patient during the neurofeedback treatment, without actual application of wet EEG electrodes, using the applied dry EEG electrodes. The simulated wet EEG signals may simulate signals that would otherwise be collected from a certain location on the head of the patient, without actually placing the wet EEG electrode at the certain location, using dry EEG signals collected from dry EEG electrodes positioned at other locations on the head of the patient.

An aspect of some embodiments of the present invention relates to systems and/or methods (e.g., code instructions stored in a storage device executed by one or more processors) that train a statistical model that outputs a simulated wet EEG signal from one or more inputted dry EEG signals. For example, the trained statistical model may be implemented as a regressor that predicts the values of the simulated wet EEG signal or a classifier that classifies the received input dry EEG signals into positive and/or negative feedback response of a neurofeedback session. The modeling of either type is determined according to measurements performed using wet EEG signals and are used for the model training. The statistical model is used during the neurofeedback treatment to provide feedback to the patient with the accuracy level of wet EEG signals, using dry EEG signals and without actually using wet EEG signals.

The statistical model is trained using data collected during administered neurofeedback treatments from one or more patients. Data is simultaneously collected from dry EEG electrodes and from wet EEG electrodes. The wet EEG electrodes are labeled as the training output set. The dry EEG electrodes are labeled as the training input set. The statistical model is trained based on mappings between the training input and training output.

An aspect of some embodiments of the present invention relates to systems and/or methods (e.g., code instructions stored in a storage device executed by one or more processors) that compute positive and/or negative feedback for a neurofeedback treatment from one or more dry EEG signals. The positive and/or negative feedback is determined with statistically significant accuracy level (i.e., within a tolerance requirement) as when computing positive and/or negative feedback using wet EEG signal(s) received from applied wet EEG electrodes, without actually applying the wet EEG electrodes, instead using dry EEG signals received from dry EEG electrodes. The positive and/or negative feedback may be determined according to a binary or discrete scale defines by classification label(s), for example defining the intensity of the positive or negative feedback. The power level of the EEG signal is translated into the classification label(s) according to classification threshold(s).

The systems and/or methods (e.g., code instructions stored in a storage device executed by one or more processors) described herein provide a technical solution to the technical problem of improving accuracy of feedback provided during neurofeedback treatments based on dry EEG signals. A simulated wet EEG signal is computed based on one or more dry EEG signals measured by respective dry EEG electrodes applied to the head of the patient. The simulated wet EEG signal is computed using the trained model without actually applying the wet EEG electrode(s) to the patient.

Abnormal brain activity, for example, related to ADHD, is sometimes best detected at medial posterior locations over the scalp, for example, from the Cz EEG channel. Measuring EEG signals is usually performed using electrolytic gels to penetrate the hair, contact the skin, and provide clean conductive signal paths. The wet EEG electrodes allow neurofeedback practitioners to use conventional EEG systems by placing the EEG electrode used for the neurofeedback treatment at locations(s) over the scalp according to the selected neurofeedback treatment and/or diagnosis. However, accurate placement of the wet EEG electrodes on the scalp and the application of the gel requires proficiency and experience from the neurofeedback practitioner, and is general cumbersome and difficult for consumers' self-delivering neurofeedback treatment at home.

Dry EEG electrodes (that do not use conducive gel) are generally designed to directly contact the scalp (or other skin), which makes the dry EEG electrodes ineffective for measurement through hair. Dry EEG electrodes cannot generally be used in place of wet EEG electrodes at the most clinically significant measurement locations on the scalp of the patient. The systems and/or methods described herein provide a technical solution to the described technical problem, by providing statistically significant accuracy of wet EEG electrodes and/or the ability to position the wet EEG electrodes on the scalp of the patient (e.g., below thick hair), with the ease of use of dry EEG electrodes, by using the measurements of the dry EEG electrodes to simulate measurements of wet EEG electrodes at certain location(s).

The systems and/or methods (e.g., code instructions stored in a storage device executed by one or more processors) described herein improve an underlying technical process within the technical field of processing EEG signals to provide feedback during a neurofeedback treatment.

The systems and/or methods (e.g., code instructions stored in a storage device executed by one or more processors) described herein improve performance by adding a new feature(s) to the computing unit that is used to apply neurofeedback treatment. The performance of the computing unit used to apply neurofeedback treatment is improved relative to existing units used to apply neurofeedback. For example, the statistical model described herein (that outputs the simulated wet EEG signal based on the inputted dry EEG signal) provide the ability to infer from dry EEG electrodes, optionally using existing processor(s) and/or available memory, the signal in the wet EEG electrode. The simulated wet EEG signal represents the brain signal of the patient in the location of the wet channel based on the dry EEG signals. The simulated wet EEG signal estimate the signal in a specific location defined for a specific neurofeedback protocol.

As described in additional detail herein, the neurofeedback protocol may be based on one or more of: the location of the wet EEG electrode, frequency bands of the treatment, the training of the user, the type of feedback, and the duration and frequency of treatment. Therefore, feedback provided to the patient based on the simulated wet EEG signal provides a more accurate and therapeutically superior feedback during the neurofeedback treatment in comparison to feedback provided based on dry EEG signals alone.

The systems and/or methods (e.g., code instructions stored in a storage device executed by one or more processors) described herein analyze data in the form of the statistical model that receives dry EEG signals and outputs simulated wet EEG signals and/or feedback instructions (based on the simulated wet EEG signals).

The systems and/or methods (e.g., code instructions stored in a storage device executed by one or more processors) described herein tie mathematical operations (e.g., computation of the trained statistical model to output the simulated wet EEG signals, and/or application of the statistical model to the dry EEG signals) to the ability of processor(s) to execute code instruction. The systems and/or methods (e.g., code instructions stored in a storage device executed by one or more processors) described herein are tied to physical real-life components, including EEG sensors.

The systems and/or methods (e.g., code instructions stored in a storage device executed by one or more processors) described herein provide a unique, particular, and advanced technique of processing dry EEG signals to compute simulated wet EEG signals for providing feedback to a patient during neurofeedback treatment.

Accordingly, the systems and/or methods described herein are necessarily rooted in computer technology to overcome an actual technical problem arising in the technical field of improvement of equipment that applies neurofeedback treatment.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term dry EEG signal(s) means EEG signals measured by dry EEG electrode(s). The dry EEG signals may be obtained from any location on the head for example, the forehead. As used herein, the term dry EEG electrode(s) means EEG electrodes that are applied to the head of the patient without using conductive gel (i.e., applied to the skin of the patient, to improve conduction of signals from the brain of the patient to the electrode(s)).

As used herein, the term wet EEG signal means EEG signals measured by wet EEG electrode(s). As used herein, the term wet EEG electrode(s) means EEG electrodes that are applied to areas of the head of the patient using conductive gel.

It is noted that the wet EEG electrodes and the dry EEG electrodes may be similar in design, with the difference being the use or lack of use of conductive gel. The wet EEG and dry EEG electrodes may be different in design, the wet EEG electrodes designed for use with conductive gel and the dry EEG electrodes designed for use without conductive gel.

As used herein, references made to the simulated wet EEG signals, for example, as outputted by the statistical model applied to the dry EEG signals, may sometimes apply to the feedback of the neurofeedback treatment. For example, the statistical model may compute the simulated wet EEG signal from the dry EEG signals. The simulated wet EEG signal may be analyzed (e.g., according to the threshold or other feedback requirement) to compute the feedback (e.g., positive, negative). Alternatively or additionally, the statistical classifier may compute the feedback from the dry EEG signals, without necessarily explicitly computing the simulated wet EEG signal. The computed feedback represents the feedback that would be obtained (within the tolerance requirement) using wet EEG signals measured using wet EEG electrodes.

As used herein, the term statistical model means a machine learning method, for example, a statistical classifier as linear discriminant analysis (LDA), a neural network, a decision tree, a set-of-rules support vector machine, k-nearest neighbor and the like, or a statistical regressor as general linear model, Bayesian regression, support vector regressor, decision tree regressor and the like.

As used herein, the neurofeedback protocol includes the following components:

1. The location of the wet EEG electrode, which may be represented by an EEG Montage (e.g., active electrode location, reference electrode location).

2. Frequency bands used for the neurofeedback treatment (e.g., alpha, theta, beta), which denotes the certain extracted and/or processed signal(s) the user is being trained to modify (e.g., power at certain frequency, power ratio between bands, phase, and/or coherence between electrode pairs).

3. What the user is being trained to do and to what extent, for example, increase or decrease the power or ratio of the raw signals, and/or frequency bands, increase or decrease the coherence between two or more channels below or above a defined threshold, for a predefined amount of time.

4. The type of feedback delivered to the user, which can be only positive (e.g. only rewarding, pleasant) when the user succeeds to produce the desired EEG measure defined in (2), only negative (e.g. only punishing, unpleasant) when the user fails to produce the desired measure, or both, positive and negative.

5. The duration and frequency of the neurofeedback treatment (e.g. the duration of each training session, how many sessions a week, for how many weeks).

The neurofeedback protocol defines the location(s) on the head for placement of the EEG electrodes. Examples of data that may be computed from the received EEG signal(s) include: the power in a certain frequency and/or frequency band (out of the available range of frequencies), manipulation(s) on certain bands (e.g., ratio between theta and beta), the phase of signal(s), and/or the coherence between pair(s) of signals (recorded from pair(s) of electrodes). The neurofeedback protocol may be defined according to the diagnosis of the user. The neurofeedback protocol is indicative of the treatment to apply to the user having the diagnosis. For example, the neurofeedback protocol for treatment of attention deficit hyperactivity disorder (ADHD) may be based on previous research, aimed to the ratio between the powers in the beta and theta bandwidths at the location of the Cz electrode. According to the ADHD neurofeedback protocol the patient's goal is to decrease the beta theta ratio. The statistical model (as described herein) is trained to simulate the power in theta and beta bands or the theta\beta ratio or other value according to the neurofeedback treatment (or the positive\negative feedback as calculated according to the ratio) as would be measured at Cz. It is noted that the statistical model may be trained to simulate the raw signal (e.g., the signal as measured from the EEG device without further processing or analysis) from the wet EEG channel, however the simulation of the certain, extracted, signal may be less accurate. The raw simulated signal may be used, for example, in other computational processes.

Figure 2:
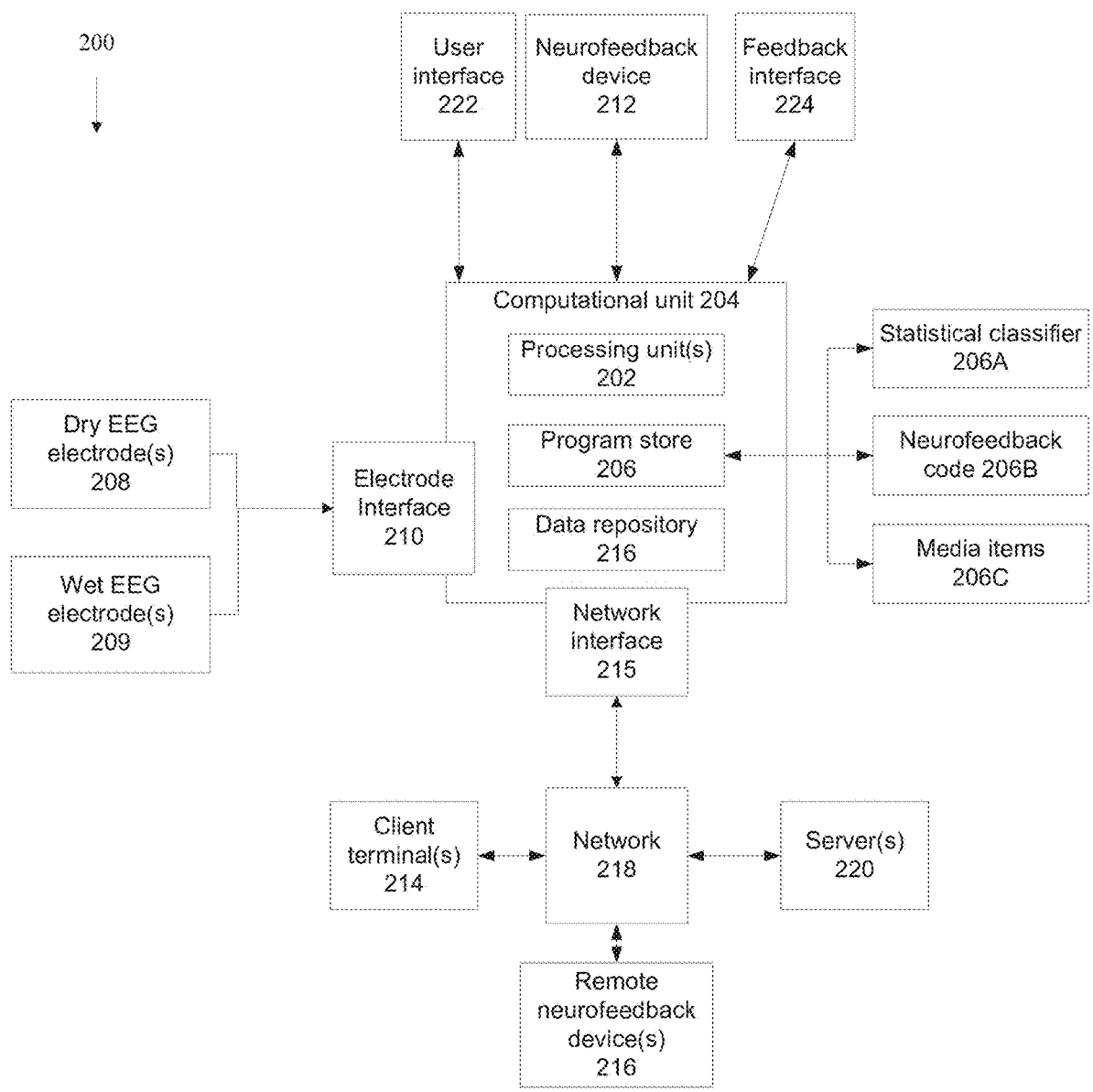
FIG. 2 is a block diagram of components of a system that trains and/or uses the statistical model that computes simulated wet EEG signals from measured dry EEG signals, in accordance with some embodiments of the present invention.

Reference is now made to FIG. 1, which is a flowchart of a method for training and/or using a statistical model that computes simulated wet EEG signals from measured dry EEG signals, in accordance with some embodiments of the present invention. Reference is also made to FIG. 2, which is a block diagram of components of a system 200 that trains and/or uses the statistical classifier that computes simulated wet EEG signals from measured dry EEG signals, in accordance with some embodiments of the present invention. System 200 may execute one or more acts of the method described with reference to FIG. 1, for example, by a processing unit 202 of a computing unit 204 executing code instructions stored in a program store 206.

System 200 includes one or more dry EEG electrodes 208 that are designed to be applied to the head of the patient without using conductive gel. Dry EEG electrode 208 may be implemented, for example, as individual electrodes each communicating with a computing device, as a headband (e.g., the MUSE™ headset available from InteraXon Inc., Toronto Canada) or other wearable structure that houses the dry EEG electrodes. Dry EEG electrodes 208 may include or be in communication with (e.g., within the wearable structure, within an intermediate computing device) hardware and/or software that performs signals processing functions, for example, signal amplification, and/or preliminary signal processing (e.g., to filter out noisy signals, such as due to eye blinking or head moving).

Computing unit 204 is in communication with dry EEG electrodes 208. Computing unit 204 may be integrated with dry EEG electrodes 208, for example, processing unit 202 and/or program store 206 are integrated within the wearable structure housing dry EEG electrodes 208. Alternatively, computing unit 204 is implemented as an external unit communicating with dry EEG electrodes 208, optionally using an electrode interface 210, for example, a physical interface (e.g., wireless communication, wire connection), and/or a virtual interface (e.g., software connection, using application programming interfaces (API), software development kit (SDK)).

Computing unit 204 may be in communication with wet EEG electrodes 209, optionally using electrode interface 210. For example, when computing unit 204 is used to compute (i.e., train) the statistical model using dry EEG signals measured by dry EEG electrodes 208 and wet EEG signals measured by wet EEG electrodes 209. It is noted that when computing unit 204 is used to deliver neurofeedback treatment using the trained statistical model, wet electrodes 209 are not necessarily used.

Computing unit 204 may be integrated with existing neurofeedback devices 212, for example, as software code instructions installed on a storage device within neurofeedback device 212 for execution by processor(s) of the neurofeedback device 212, as hardware that is inserted into an interface in neurofeedback device 212, and/or as an external unit that connects to neurofeedback device 212 (e.g., using a data interface). Alternatively or additionally, neurofeedback device 212 may be implemented as components (e.g., hardware, software, firmware) within computational unit 204, for example, as code stored in program store 206 and/or data repository 216 executed by processing unit(s) 202. For example, computing unit 204 may compute the simulated wet EEG signal that is provided to neurofeedback device 212 (instead of actual wet EEG signals measured by actual applied wet EEG electrodes), computing unit 204 may provide feedback instructions for execution by neurofeedback device 212, or other architectures may be implemented.

Computing unit 204 may be implemented as, for example, a client terminal, a server, a mobile device, a desktop computer, a thin client, a Smartphone, a Tablet computer, a laptop computer, a wearable computer, glasses computer, and a watch computer. Computing unit 204 may include locally stored software that performs one or more of the acts described with reference to FIG. 1, and/or may act as one or more servers (e.g., network server, web server, a computing cloud) that provides services (e.g., one or more of the acts described with reference to FIG. 1) to one or more client terminals 214 and/or remotely located neurofeedback devices 216, for example, providing software as a service (SaaS) to client terminal(s) 214 and/or remotely located neurofeedback devices 216, providing an application for local download to client terminal(s) 214 and/or remotely located neurofeedback devices 216, and/or providing functions using a remote access session to client terminals 214 and/or remotely located neurofeedback devices 216, such as through a web browser.

Processing unit 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processing unit(s) 202 may include one or more processors (homogenous or heterogeneous), which may be arranged for parallel processing, as clusters and/or as one or more multi core processing units.

Program store 206 stores code instructions implementable by processing unit 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Program store 206 may store code instructions that execute one or more acts of the method described with reference to FIG. 1.

Computing unit 204 may include a data repository 216 for storing data. Data repository 216 may be implemented as, for example, a memory, a local hard-drive, a removable storage unit, an optical disk, a storage device, and/or as a remote server and/or computing cloud (e.g., accessed using a network connection). It is noted that code instructions executable by processing unit 202 may be stored in data repository 216, for example, with executing portions loaded into program store 206 for execution by processing unit 202.

Program store 206 and/or data repository 216 may store the trained statistical model 206A (that computes the simulated wet EEG signal as described herein), neurofeedback code 206B that provides the administered neurofeedback according to the neurofeedback protocol (i.e., calculate whether positive or negative feedback should be given), and/or media items 206C that are adjusted during the neurofeedback treatment based on the computed simulated wet EEG signal. Exemplary media items 206C include still images, videos, games, and sound (e.g., music, audio files, radio, sound associated with videos and/games).

Computing unit 204 may include a network interface 215 for connecting to a network 218, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing unit 204 may access one or more remote servers 220 using network 218, for example, to download the statistical classifier 206A, and/or to provide the statistical classifier 206A (when computing unit 204 is used to train statistical classifier 206A) for download.

Computing unit 204 includes and/or is in communication with one or more user interfaces 222 allowing a user to enter data (e.g., select the neurofeedback protocol parameters, enter data for the current session) and/or view presented data (e.g., summary of the administered neurofeedback treatment). Exemplary user interfaces 222 include, for example, one or more of, a touchscreen, a display, a keyboard, a mouse, and voice activated software using speakers and microphone.

Computing unit 204 includes and/or is in communication with one or more feedback interfaces 224 that present media according to the neurofeedback protocol. The media is adjusted as feedback to the patient being administered the neurofeedback treatment according to the computed simulated wet EEG. Exemplary feedback interfaces 224 include a display for presenting images, video, and/or video games, and speakers for playing sound such as music, audio files, and the sound associated with the presented images, video, and/or video games.

The acts of the method described with reference to FIG. 1 may be stored as program code instructions in program store 206, executable by processing unit 202 of computing unit 204.

At 101, dry electrode(s) 208 are applied to the patient. The dry EEG electrodes are positioned on the head (e.g. scalp, forehead) of the patient at locations corresponding to the temporal and/or frontal lobe, for example, at one or more of the following EEG channels based on the 10-20 standard: Fpz, Fp1, Fp2, F3, F4, Fz, F7, F8, T3, T4, Tp9, Tp10, and intermediate locations thereof. The dry EEG electrodes may be positioned at locations without hair.

Dry EEG electrode(s) 208 may be applied according to available equipment, optionally independently of any predefined location for example, according to the positions of the electrodes on a headset. For example, at locations TP9, FP1, FP2, AF7, AF8, and TP10.

Reference electrodes may be applied, for example, on the ear lobe, and/or at Fpz.

Optionally, wet EEG electrode(s) 209 are applied to the patient. The wet EEG electrodes are applied during training of the statistical model. The wet EEG electrodes are not applied during use of the statistical model to administer neurofeedback treatment to the patient. The wet EEG electrodes are positioned at locations corresponding to central, and/or parietal lobe, and/or occipital lobe. For example, at one or more of the following EEG channels based on the 10-20 standard: C3, C4, Cz, P3, Pz, P4, O1, Oz, O2, and intermediate locations thereof. The wet EEG electrodes may be positioned at locations that normally have growing hair.

Wet EEG electrode(s) 209 may be applied according to a predefined protocol, at the location that is selected when the neurofeedback treatment is normally administered (i.e., using standard methods). For example, the Cz location may be selected.

The dry EEG electrodes are placed in locations that are non-overlapping with locations of wet EEG electrodes.

Dry EEG electrode(s) 208 are applied without conductive gel. Wet EEG electrode(s) 209 are applied using conductive gel.

Figure 5:
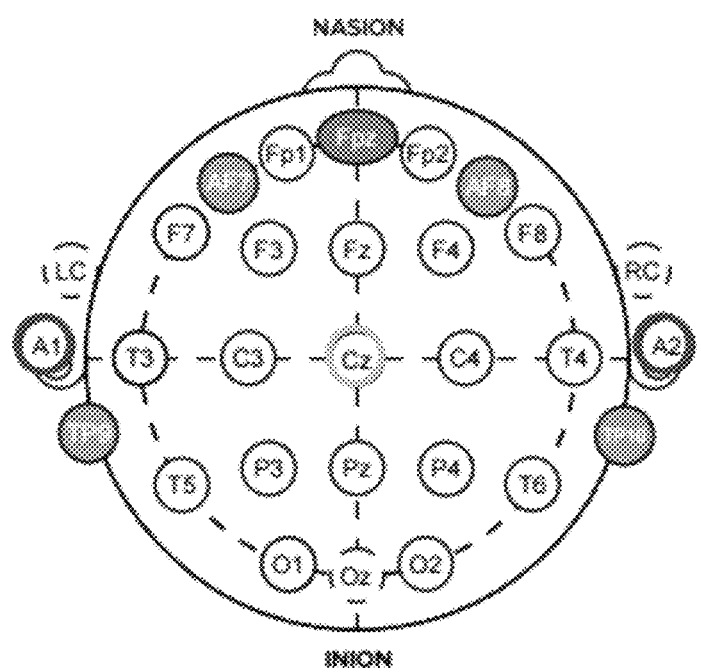
FIG. 5 is a schematic depicting exemplary locations for placement of the dry and/or wet EEG electrodes on the head of the patient, in accordance with some embodiments of the present invention.

Reference is now made to FIG. 5, which is a schematic depicting exemplary locations for placement of the dry and/or wet EEG electrodes on the head of the patient, in accordance with some embodiments of the present invention. The locations are defined according to 10-20 international standards.

An exemplary location for the dry reference channel electrode (e.g., based on the MUSE™ headset) is Fpz.

Exemplary locations for dry active channel electrodes (e.g., based on the MUSE® headset) include: TP9, AF7, AF8, and TP10.

An exemplary location for the wet auxiliary active channel electrode is Cz. Exemplary locations for the wet auxiliary reference channel include: A1, and A2.

It is noted that the arrangement of electrodes describes with reference to FIG. 5 is optional, and described as an example which is not necessarily limiting, as other electrode placement arrangement may be used, for example, custom designed arrangement and/or arrangements based on other standards. For example, the depicted Cz electrode is shown as an example. Other electrode locations may be used.

Referring now back to FIG. 1, at 102, a statistical model that computes a simulated wet EEG signal from one or more dry EEG signals is trained. Alternatively or additionally, the statistical model that outputs instructions for adjusting feedback of the neurofeedback session is computed, where the feedback is based on the simulated wet EEG signal computed based on one or more dry EEG signals.

For clarity and simplicity, the case of the model classifier computing one simulated wet EEG channel is described. However, it is understood that the statistical model, or multiple statistical models may be trained to generate multiple simulated wet EEG signals that estimate wet EEG electrodes placed at different locations on the head. As used herein, the terms training and computed are sometimes interchanged when referring to the statistical model.

The statistical model may be trained at a central location, for example, at a computing unit of the manufacturer. Training may be performed based on data collected from multiple patients, optionally having one or more diagnoses, and administered one or more neurofeedback treatments. The computed (i.e., trained) statistical models may be provided to each local computing unit of consumers (or local neurofeedback practitioners), for example, by being stored in the program store of a neurofeedback computing unit that is newly purchased, and/or by downloading the statistical classifier from the server of the manufacturer. Local computing units may receive periodic updates of the statistical model. Alternatively, the statistical model may be trained for a certain patient, using data of the patient. The statistical classifier trained using the data collected from the certain patient may be used by the certain patient for neurofeedback treatments.

Models may be trained, for example, per diagnosis, per neurofeedback protocol, per wet EEG electrode location, and/or generally (e.g., for different diagnoses, and/or neurofeedback protocols).

Figure 3:
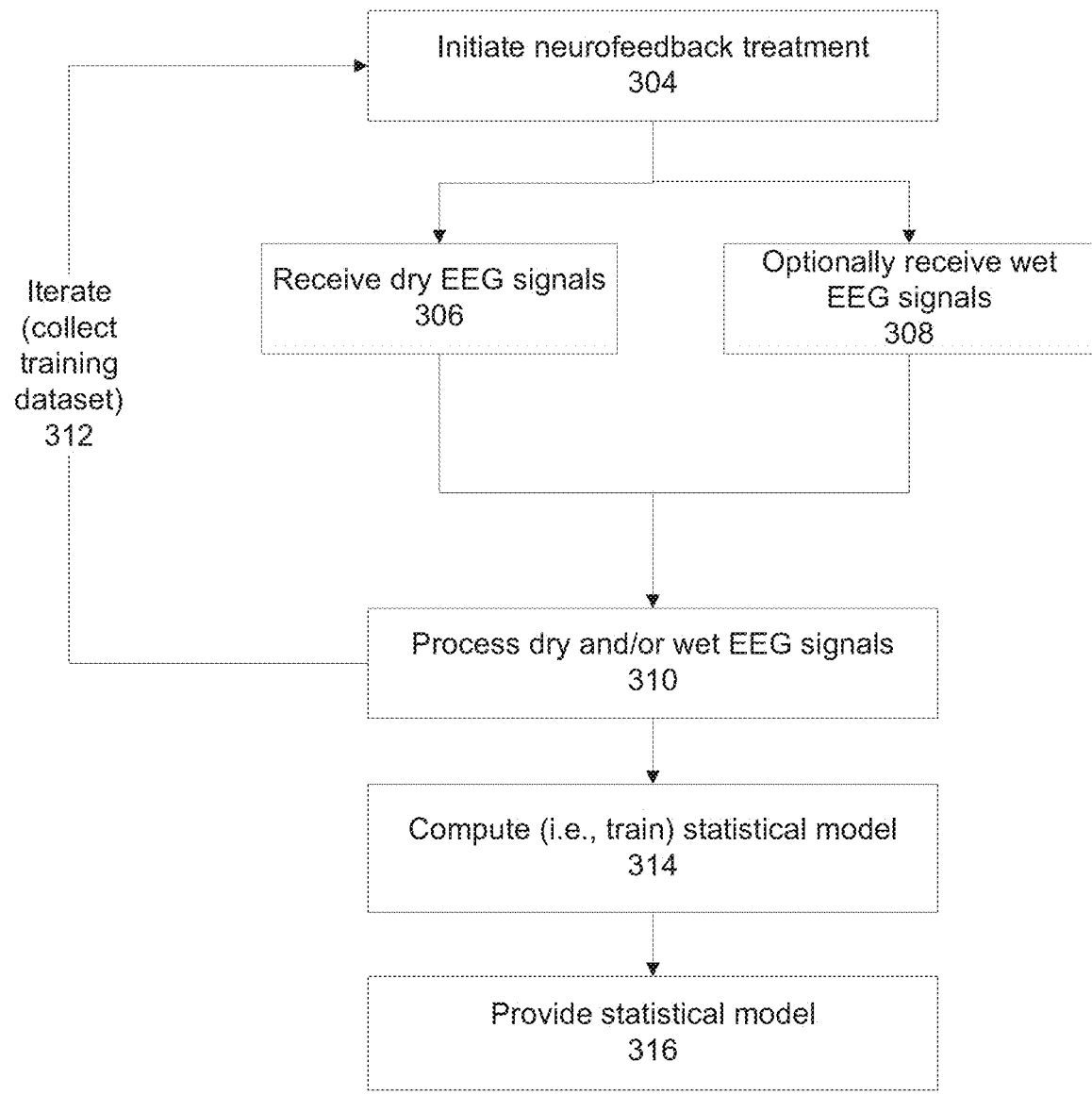
FIG. 3 is a flowchart of a method for computing/training the statistical classifier, in accordance with some embodiments of the present invention.

Reference is now made to FIG. 3, which is a flowchart of a method for training the statistical model, in accordance with some embodiments of the present invention. The acts of the method described with reference to FIG. 3 may be stored as program code instructions in program store 206, executable by processing unit 202 of computing unit 204. It is noted that computing unit 204 may be implemented as part of a neurofeedback device operated locally by the patient and/or the neurofeedback practitioner, and/or computing unit 204 may be implemented as a central server operated by the manufacturer or other organization that centrally trains the statistical model for distribution to local neurofeedback units.

At 304, neurofeedback treatment is initiated. The neurofeedback treatment may be administered as would otherwise be administered when the statistical model is not being trained, for example, the neurofeedback treatment is selected according to the diagnosis of the patient. For example, patients diagnosed with ADHD, are guided using feedback based on changing calculated theta/beta power EEG measures from Cz. The aim of the neurofeedback treatment administered to the ADHD patients is to reduce the power of the theta frequency band (4-7 Hertz(Hz)) and/or increase the power of the SMR frequency band (12-16 Hz), and/or beta frequency band (16-20 Hz). Data may be collected from multiple patients, each undergoing one or more training days during which one or more training sessions are administered (e.g., each session length being about 20-40 minutes, where each session includes multiple rounds each about 3-5 minutes).

One or more media items are adjusted according to sensed EEG signals of the brain of the patient being administered the neurofeedback treatment, according to the administered neurofeedback protocol. The feedback may be positive feedback in response to the performance of the patient, for example, inaudible sound becomes louder, and a blurry video becomes sharp. The feedback may be negative in response to the performance of the patient, for example, loud sound becomes inaudible, or a sharp video becomes blurry.

At 306, dry EEG signal(s) measured by respective dry EEG electrodes 208 applied to the head of the patient are received, optionally by computing unit 204 through electrode interface 210.

At 308, wet EEG signal measured by respective wet EEG electrode(s) 209 applied to the head of the patient are received, optionally by computing unit 204 through electrode interface 210.

The wet EEG and the dry EEG signals may be simultaneously received during the administered neurofeedback treatment.

At 310, the received dry EEG and/or wet EEG signals are processed.

Optionally, the received dry EEG and/or wet EEG signals may be processed to remove artifacts and/or noisy segments, for example, due to eye blinking, bad contact, and/or head movement. The received dry EEG and/or wet EEG signals may be processed by conversion from analogue to digital representation. The received dry EEG and/or wet EEG signals may be processed by referencing to the respective reference channels. The received dry EEG and/or wet EEG signals may be processed by scaling the signals to a common scale.

Alternatively, or additionally, the received dry EEG and/or wet EEG signals may be processed using time frequency analysis (i.e., transformation to the time-frequency domain) methods to extract frequency oscillation power values over time. The frequency values may be used as labels of the EEG signals for training the statistical model. For example, oscillation power in the range of 1-30 Hz may be calculated from consecutive duration time windows (e.g., about 1 second or 5 seconds, or other times values), for example, using Fast Fourier Transform, Wavelet or multitaper signal processing method.

The frequency oscillation power values extracted from the channels of the dry EEG and/or wet EEG may be averaged into frequency bands. Exemplary frequency bands are according to different biological significance that are utilized for neurofeedback, including: theta (4-7 Hz), alpha1 (8-10 Hz), alpha2 (11-13 Hz), beta1 (12-15 Hz), and beta2 (16-25 Hz).

Alternatively, or additionally, the received dry EEG and/or wet EEG signals are processed to create training datasets for training the statistical model. The received dry EEG data may be tagged as input training data. The wet EEG signals may be tagged as output training data. The association with frequency bands may be used for computing the statistical model.

Optionally, a classification threshold(s) are computed based on the administered neurofeedback protocol. A classification threshold may be computed, for example, based on continuous power of the wet EEG channel, a defined power ratio of the wet EEG channel, according to a predefined success rate of the user, and/or other methods. When defined according to success rate, for example, of 60%, the classification threshold is set to the value that the user remains above or below (according to the neurofeedback protocol), 60% of the time. This time, aimed to set the threshold, takes about one minute, normally before each neurofeedback session. The classification threshold sets the type of feedback (positive or negative) and is used for adjustment of the media item according to the administered neurofeedback protocol.

The classification threshold(s) may be binary or gradual (e.g., for a set of classification levels). For example, in the case of a positive feedback, when the patient reaches the predefined signal threshold or above it (according to the protocol), it is indicative that the user receives a positive feedback (i.e., higher quality or better behavior of the media item) otherwise, the current state is maintained (i.e., current quality or behavior of the media item). In another example, based on a negative feedback, if the patient does not reach the predefined signal threshold, it is indicative that the user receives a negative feedback (i.e., lower quality or worse behavior of the media item). The feedback, either positive or negative, may be gradually adjusted to be weak or strong according to the statistical distance from the threshold, or binary according to whether it's below or above the threshold.

The classification threshold(s) may be computed based on the frequency bands. For example, to provide feedback for patients being administered to neurofeedback treatment for ADHD, the baseline theta\beta power ratio measured in the wet EEG channel Cz may be used to compute the classification threshold(s). It is noted that feedback may be determined using two separate frequencies rather than or in addition to the ratio calculation, for example, when theta is below a first threshold, and beta is above a second threshold, the feedback is positive and/or otherwise feedback is negative.

In an example of using the computed ratio with one threshold, attenuation of the theta\beta ratio in the Cz channel below the classification threshold is associated with a first out of two classification labels indicative of reward (i.e. delivering positive feedback, for example, adjustment of a movie to a higher visual quality or earning more points in a computer game). Enhancement of the theta\beta ratio above the classification threshold is associated with a second out of two classification labels indicative of punishment (i.e. delivering negative feedback, for example, adjustment of the movie to lower visual quality or loosing points in a computer game). In an example of using the computed ratio with multiple thresholds, attenuation of the theta\beta ratio in the Cz channel below the lowest classification threshold is associated with the first out of N labels indicative of the highest degree of reward. Enhancement of the theta\beta ratio above the highest classification threshold is associated with the N classification label indicative of lowest degree of reward (or highest degree of punishment).

Optionally, the continuous computation based on the frequency bands (e.g., theta\beta power values) is translated to discrete classification labels according to the classification threshold(s), for example, binary labels, positive or negative feedback (0 or 1) when one threshold is used, or more ordinal labels, weaker or stronger feedbacks (0, 1, 2, ..., N) when N thresholds are used.

The classification threshold(s) may be indicative of, for example, positive or negative, stronger or weaker feedbacks for the neurofeedback treatment being administered to the patient. The classification labels (e.g., binary values such as 0 and 1, or discrete N values ranging from 1 to N) represent an estimate of whether the signal is above or below certain threshold(s) applied to the simulated wet EEG signal within the tolerance requirement of the actual wet EEG signal. The power level of the EEG signal is translated into the classification label(s) according to the classification threshold(s).

Exemplary binary classification labels include binary values, for example, 0 or 1, TRUE or FALSE.

It is noted that for multiple classification labels, other scales may be used for the classification threshold, for example, various levels of feedback, for example, a three levels scale of the quality of the media item, for example, poor quality, medium quality, and high quality. Other scales with a larger number of classification categories may be used. In such cases (i.e., above 2 classification categories) the classification threshold may be referred to as a classification requirement, or classification categories.

The classification thresholds may be calculated, for example, based on the frequency bands (e.g., theta\beta power ratio) from the first portion of the measured EEG signals (e.g., the first minute), optionally before initiation of the neurofeedback treatment.

The classification label(s) may be computed per time window of the administered neurofeedback treatment, for example, per predefined time interval (e.g., 0.25, 0.3, 0.5 second, 1 second or other lengths of time window). In the case of binary labels, time windows associated with a positive label computed based on the wet EEG signal (e.g., above the classification threshold) are assigned with positive classification label.

The classification threshold may be used as additional training parameter for training the statistical model when this model is a classifier (i.e. output classification labels and not continuous values). A trained statistical classification model may compute and output the label of new time windows according to the signal values (e.g. frequency band power) of the dry EEG signal(s). Additional details of training the statistical classifier are described herein, for example, with reference to block 314.

At 312, one or more acts described with reference to blocks 304-310 are iterated. The iterations may be performed, for example, for different patients, for different locations on the head, for different neurofeedback protocols, and/or for different diagnosis. The iterations may be performed, for example, for the same patient for multiple neurofeedback protocols.

The iterations are designed to collected sufficient data to provide a suitable training dataset to train a statistically significant classifier.

An exemplary method for creating the training dataset for training the statistical model is now described. The received EEG signal(s) are processed to create an input matrix (or other structural data representation) based on dry and wet EEG channels with the form of samples X features, and an input vector based on the wet channel with the length of according to the number of samples. Optionally, a feature space is created. The feature space may be used to populate the input matrix of the training dataset for training the statistical model, as described in the paragraph below. The feature space express characteristics based on the data collected from each patient. It may include the power estimated from each frequency band, for each dry and/or wet EEG channel. The feature space may be defined as: [T]×[Ch]×[Fr], where the wet EEG signal in wet EEG channel Cz in time window T may be simulated based on dry EEG frequency bands Fr intensities in dry EEG electrode channels Ch at time window T.

In one example, each row denotes one sample, optionally one time window, for example, corresponding to a window of length 0.5 seconds, or 1 second, or other time lengths, and the columns denote the feature space. In another example, the rows denote the feature space, and the columns denote the samples. In yet another example, a map stores mappings between the samples and features, for example, as a set of pointers. The map may be stored as a separate data structures that maps between the data structure storing the samples and the data structure storing the features. The feature space is based on the description in the previous paragraph. Each feature is power at a [T]×[Ch]×[Fr] as calculated based on the specific time window. An output vector of the training set is created based on the wet channel EEG (having the same size of samples) of the input matrix. The output vector represents the desired simulation from the wet EEG channel (e.g., the power ratio or the label).

It is noted that additional features representing brain activity at each dry EEG electrode and/or at each frequency band may be added from previous successive time windows. Based on the assumption that time dependency exists between successive time windows, the additional information may further improve the accuracy of simulation of the wet EEG channel at time T.

At 314, the statistical model is trained based on the collected training dataset and the constructed feature space based on processing of raw data. The statistical model is trained using the dry EEG signal(s) as input training data, and the wet EEG signal(s) as output training data. The computed signals in the wet EEG electrode(s) (e.g., the theta\beta power ratio), or the labels computed according to the classification threshold, provides the output to the training data. It is noted that there may be a single classification threshold (or classification requirement) per time interval (the same classification threshold may be used for multiple time intervals), optionally for the first portion (e.g., first minute) of the signal recording of the time interval.

The statistical model is trained to simulate the wet EEG signal(s) that would otherwise be measured at the selected wet EEG electrode location, based on dry EEG signal(s) according to a tolerance requirement. The tolerance requirement may be indicative of the amount of statistical error that may exist between the simulated wet EEG signal(s) and the measured wet EEG signal(s). The tolerance requirement may be selected, for example, according to clinical relevance (e.g., the simulated wet EEG signal produces clinically similar feedback in comparison to the actual wet EEG signal) and/or according to statistical significance (e.g., the simulation of the actual wet EEG signal is statistically significant).

Optionally, the simulated wet EEG signal is computed as a weighted combination of the dry EEG signals.

Optionally, multiple statistical models are trained using different classification and/or regression machine learning methods. The statistical model that outputs the most accurate simulated wet EEG and/or has the highest probability of correct output may be selected from the multiple statistical models. Each of the statistical models may be trained based on a first portion (in terms of time) of the training dataset (i.e., wet EEG and the dry EEG signals), for example, the first 15 minutes of a 30 minute neurofeedback treatment session. The statistical models may be selected from the multiple computed (i.e., trained) statistical models according to a probability of accurate prediction within the tolerance requirement using the remaining portion of training data, for example, applying each of the multiple statistical models to the remaining 15 minutes of the 30 minute neurofeedback protocol session, and evaluating the output of each statistical models relative to the actual training data.

It is noted that the first portion of the EEG signal may be used for the training dataset and for the threshold calculation may be the same first portion, or different first portions may be used for the training dataset and for the threshold calculation.

Optionally, the statistical model is trained based on a feature space using power measured at each of multiple frequency bands and\or on previous time windows compute for each of the measured dry EEG signals per time interval.

An example for a statistical model that can be applied is the linear discriminant analysis (LDA). The LDA is a classifier that may be trained for each neurofeedback treatment session of each patient or to generalize for all treatment. The LDA model may be used to predict (i.e. simulate) the classification value (e.g., indicative of feedback positive or negative feedback) of the wet EEG channel. LDA models the class conditional distribution of the data P(X|y=k) for each class k. Predictions (i.e., simulations) may be obtained using B aye's rule:

$$P(y \mid X) = P(X \mid y) \cdot P(y)/P(X) = P(X \mid y) \cdot P(Y) \Big/ \left( \sum_{y'} P(X \mid y') \cdot p(y') \right)$$

where P(X|y) is modeled as a Gaussian distribution. The Gaussians for each class are assumed to share the same covariance matrix, leading to a linear decision surface, which may be obtained by comparing the log-probability ratios: log [P(y=k|X)/P(y=l|X)].

The LDA model is simple in the sense the mode has no hyper parameters that need to be fine-tuned and optimized.

In models that are more complex the combination of model parameters may be optimized by considering the possible combinations of parameters and selecting the combination that yields the model with best performance. As described herein, cross validation schemes may be implemented on the training set, and after model selection, evaluation on the test set may be made.

At 316, the statistical model is provided for computing the simulated wet EEG signal. The statistical model may be used on other patients (i.e., other than the ones used to train the statistical model). The statistical model may be stored and/or transmitted. For example, the created statistical model (computed by a server) is distributed for use in local clinics and/or at home. Alternatively, the statistical model may be created per patient, for example, the statistical classifier is trained at a designated facility with the help of a technician or practitioner to apply the wet EEG electrodes, and the patient may use the trained statistical classifier alone at home using the dry EEG electrodes.

Referring now back to FIG. 1, at 104, the statistical model is applied during administration of a neurofeedback treatment to a patient. The statistical classifier receives measured dry EEG signals, and outputs a simulate EEG signal and/or feedback instructions for adjusting feedback of the neurofeedback session based on simulated EEG signals.

Figure 4:
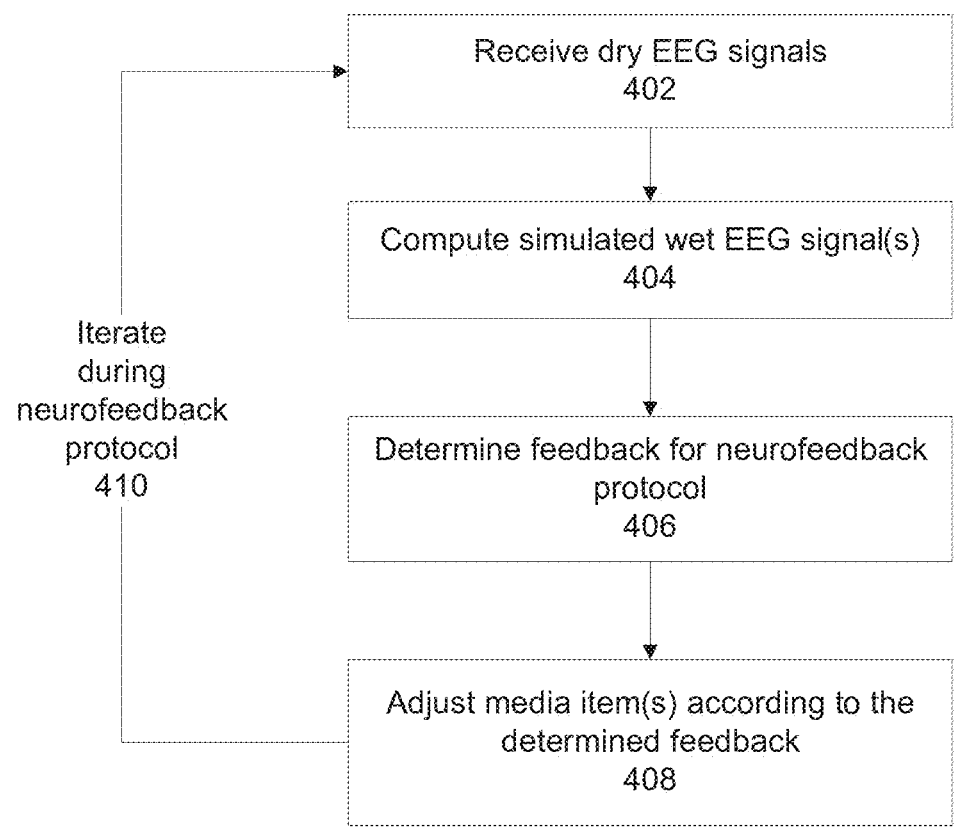
FIG. 4 is a flowchart of an exemplary method for applying the statistical classifier, in accordance with some embodiments of the present invention.

Reference is now made to FIG. 4, which is a flowchart of an exemplary method for applying the statistical model, in accordance with some embodiments of the present invention. The acts of the method described with reference to FIG. 4 may be stored as program code instructions in program store 206, executable by processing unit 202 of computing unit 204. It is noted that computing unit 204 may be implemented as part of a neurofeedback treatment device operated locally by the patient and/or the neurofeedback practitioner using the trained statistical classifier.

At 402, dry EEG signal(s) measured by respective dry EEG electrodes 208 applied to the head of the patient during application of the neurofeedback treatment are received, for example, by computing unit 204 using electrode interface 210.

Optionally, dry EEG electrodes 208 are located at the frontal and/or temporal locations on the head of the patient (optionally locations without hair). The location of dry EEG electrodes 208 may be defined by the location of the dry EEG electrodes used on patients during training of the statistical classifier, for example, using headsets housing EEG electrodes at defined positions.

Optionally, the dry EEG signals are measured from one or more of the following locations: Tp9, Fp1, Fp2, AF7, AFB, and Tp10.

At 404, simulated wet EEG signal(s) are computed by applying the trained statistical model to the received dry EEG signals. The simulated wet EEG signal is computed within the tolerance requirement based on what an actual wet EEG electrode placed at a designated location (i.e., corresponding to the location where the wet EEG electrode was positioned during training of the statistical model) would measure as actual wet EEG signals.

It is noted that the wet EEG signals may be directly computed by the trained statistical model for use in computing the neurofeedback instructions for adjusting the media item(s). Alternatively, the wet EEG signals are implicitly and/or indirect computed when the trained statistical model outputs the neurofeedback instructions for adjusting the media item(s) (as described with reference to block 406).

The simulated wet EEG signals is an estimate of the actual wet EEG signal measured at the Cz EEG channel, or other EEG channel locations over hair covered scalp.

The simulated wet EEG signal is an estimate of the actual wet EEG signal without actually applying the actual wet EEG electrode to a location defined by the neurofeedback protocol.

Optionally, the simulated wet EEG signal is determined according to a neurofeedback protocol administered to the patient defining the location of the actual wet EEG electrode, the signal the patient should train to modify (e.g. power at a specific frequency band, a power ratio between frequency bands, the phase of the signal etc. Using the statistical model neurofeedback treatments that would otherwise not be suitable for delivery without wet EEG electrodes (e.g., to hair covered regions of the scalp) may be administered to the patient.

The simulated wet EEG signal estimates the actual wet EEG signal measured by the actual wet EEG electrode applied to the head using conductive gel, optionally at a location on the head having hair (i.e., at a location which is unsuitable for placement of a dry EEG electrode).

At 406, feedback for the neurofeedback treatment is determined. The determined feedback may be provided by neurofeedback code 206B and/or to neurofeedback device 212 and/or to remote neurofeedback device 216.

The feedback is determined according to a determined classification label based on a classification threshold (or classification requirement) applied to the simulated wet EEG signal, or based on the direct prediction of the classification model. The classification label serves as instructions for a neurofeedback system (e.g., neurofeedback device 212) to adjust the media item as feedback for the neurofeedback protocol administered to the patient. For example, a classification label of 0 denotes high quality video and/or loud sound, and a classification value of 1 denotes blurry video and/or low volume sound.

The trained statistical model may be applied to the dry EEG signals to compute the classification label. Alternatively or additionally, the classification label is computed by applying the classification threshold to the simulated EEG signals.

The classification label is indicative of positive feedback and/or negative feedback and/or no change in feedback for the neurofeedback treatment being administered to a patient.

The trained statistical model may map a set of values defined in the feature space (e.g., power at frequency band, an interaction between frequency bands (e.g., ratio), phase, coherence in one or more dry channels from the current or previous time windows) to a classification label of the simulated wet EEG channel, per time window. The classification label may be determined according to the predefined threshold indicative of positive or negative response to the neurofeedback treatment.

At 408, the media item(s) (e.g., media item(s) 206C) may be adjusted (e.g., by neurofeedback code 206B and/or neurofeedback device 212 and/or remote neurofeedback device 216) according to the determined feedback instructions based on the classification label. The adjustment of the media item is used to provide feedback to the patient as per the administered neurofeedback protocol. The adjustment may be based on positive feedback and/or negative feedback.

At 410, one or more of blocks 402-408 are iterated dynamically during the neurofeedback treatment, using measured dry EEG signal(s) to determine instructions to adjust media items serving as feedback for the patient undergoing the neurofeedback treatment.

Figure 6:
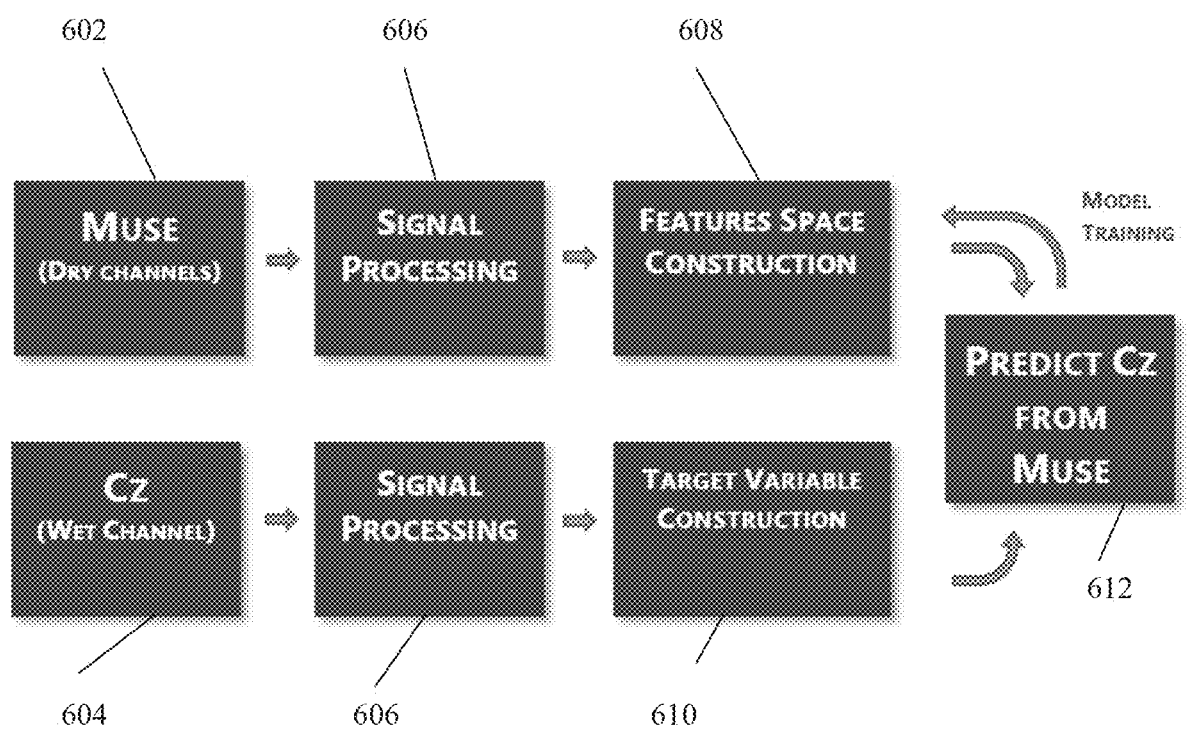
FIG. 6 is a dataflow flow diagram depicting exemplary dataflow for computing the simulated wet EEG signals, in accordance with some embodiments of the present invention.

Reference is now made to FIG. 6, which is a dataflow flow diagram depicting exemplary dataflow for computing the simulated wet EEG signals, in accordance with some embodiments of the present invention. The dataflow diagram described with reference to FIG. 6 may be implemented as part of the method described with reference to FIG. 1 (and/or FIG. 3 and/or FIG. 4), and/or executed by system 200 described with reference to FIG. 2.

Block 602 denotes receiving dry EEG signals measured by dry EEG electrodes (e.g., using the MUSE™ headband available from InteraXon Inc. of Toronto, Canada) applied to the patient. The dry EEG signals may be referenced to the Fpz channel. Block 602 is executed simultaneously with block 604 that denotes receiving wet EEG signals measured by wet EEG signals applied to the patient, for example, the Cz channel referenced to the ear. Block 606 denotes signal processing of the wet EEG signals and dry EEG signals, for example, artifact removal and/or time-frequency analysis. Block 608 denotes creation of the feature space based on the dry EEG signals, which is used as the input for the training dataset. Block 610 denotes computation of the target variable, optionally determination of the positive or negative feedback to be administered to the patient, which is used as the output for the training dataset. Block 612 denotes training of the statistical model using the input and output training datasets. The trained statistical model simulates the wet EEG signal (i.e. Cz) using dry EEG signals (i.e., based on muse).

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant neurofeedback devices and EEG electrodes will be developed and the scope of the terms neurofeedback device and EEG electrode are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for adjusting a feedback of a neurofeedback treatment according to a simulated wet electroencephalogram (EEG) signal computed by a trained statistical model based on dry EEG signals, comprising:

receiving at least one dry EEG signal measured by at least one dry EEG electrode applied to at least one location on a head of a patient corresponding to at least one of temporal lobe or frontal lobe;

computing at least one simulated wet EEG signal by applying a trained statistical model based on the at least one dry EEG signal, the at least one simulated wet EEG signal is an estimate of respective wet EEG signals measured by at least one wet EEG electrode applied to at least one location corresponding to at least one of: central, parietal lobe, and occipital lobe; and adjusting, according to the at least one simulated wet EEG signal, at least one media item presented to the patient as feedback during a neurofeedback treatment administered to the patient by a neurofeedback device.

2. The method of claim 1, wherein the at least one dry EEG electrode is applied to at least one location on the head of the patient which is not covered with hair, and the at least one simulated wet EEG signal simulates measurements performed at least at one location on the head of the patient which is covered with hair.

3. The method of claim 1, wherein the locations of the at least one dry EEG electrode and the at least one wet EEG electrode denoting the location of the at least one simulated wet EEG signal are non-overlapping.

4. The method of claim 1, wherein the at least one dry EEG signal is received during application of the neurofeedback treatment without actually applying the at least one wet EEG electrode.

5. The method of claim 1, wherein the at least one simulated wet EEG signal denotes a location on the head of the patient unsuitable for placement of the at least one dry EEG electrode.

6. The method of claim 1, wherein the at least one simulated wet EEG signal is an estimate of a wet EEG signal measured at one or more EEG channels selected from the group consisting of: C3, C4, Cz, P3, Pz, P4, 01, Oz, 02, and intermediate locations thereof.

7. The method of claim 1, wherein the at least one dry EEG signal is measured from one or more EEG channels selected from the group consisting of: Fpz, Fp1, Fp2, F3, F4, Fz, F7, F8, T3, T4, Tp9, Tp10, and intermediate locations thereof.

8. The method of claim 1, wherein the at least one simulated wet EEG signal is an estimate of a wet EEG signal measured at the Cz EEG channel, and the at least one dry EEG signal is measured from at least one member selected from the group consisting of: Tp9, Fp1, Fp2, AF7, AF8, and Tp10.

9. The method of claim 1, further comprising computing a classification label based on a classification threshold applied to the at least one simulated wet EEG signal, the classification label used by a neurofeedback device to adjust at least one media item according to a neurofeedback protocol administered to the patient.

10. The method of claim 1, wherein the location for placement of a wet EEG electrode corresponding to the at least one simulated wet EEG signal is determined according to a neurofeedback protocol administered to the patient, wherein the wet EEG electrode is not actually applied to the patient.

11. The method of claim 1, wherein the trained statistical model maps a plurality of set of values of a feature space corresponding to at least one dry EEG channel to a classification label of the at least one simulated wet EEG channel at each time window, wherein the classification label is determined according to a predefined classification threshold indicative of positive or negative feedback to the neurofeedback treatment.

12. The method of claim 1, wherein the at least one simulated wet EEG signal estimates a corresponding actual wet EEG signal as would have been measured by at least one actual wet EEG electrode applied to the head using conductive gel.

13. The method of claim 1, wherein the at least one simulated wet EEG signal estimates a corresponding actual wet EEG signal measured by at least one actual wet EEG electrode having a location on the head of the patient which is covered with hair.

14. A method for application of a neurofeedback treatment based on a simulated wet electroencephalogram (EEG) signal computed from at least one dry EEG signal, comprising:

receiving at least one dry EEG signal measured by at least one dry EEG electrode applied to locations on a head of a patient corresponding to at least one of temporal lobe and frontal lobe;

applying a trained statistical model to the at least one dry EEG signal to compute a classification label indicative of at least one of: positive feedback and negative feedback for a neurofeedback treatment being administered to a patient, the classification label represents an estimate of whether a signal is above or below a classification threshold applied to at least one wet EEG signal measured by at least one wet EEG electrode at a location defined by the neurofeedback protocol corresponding to at least one of: central, parietal lobe, and occipital lobe;

applying the trained statistical model to compute at least one simulated wet EEG signal based on the at least one dry EEG signal;

determining a classification label of the at least one simulated wet EEG signal; and adjusting at least one media item presented to the patient as feedback during the neurofeedback treatment administered to the patient according to the determined classification label indicating at least one of: the positive feedback and negative feedback.

15. The method of claim 14, wherein the at least one wet EEG signal and the at least one dry EEG signal are simultaneously received during a neurofeedback treatment administered to the patient.

16. The method of claim 14, further comprising computing at least one classification label based on a classification threshold, the classification label is indicative of feedback for an administered neurofeedback treatment based on adjustment of at least one media item, wherein computing the statistical model comprises computing the statistical model using the at least one classification label as the output training data.

17. The method of claim 14, wherein time windows assigned with positive labels are computed based on the at least one wet EEG signal above a classification threshold indicative of a rewarding setting of feedback adjustment according to the neurofeedback protocol, and other time windows including negative values computed based on the at least one wet EEG below the classification threshold indicative of a punishing setting of the feedback adjustment according to the neurofeedback protocol, and wherein the statistical model is computed to output the positive or negative classification label according to the at least one dry EEG signal.

18. The method of claim 14, wherein the at least one simulated wet EEG signal is computed as a weighted combination of a plurality of dry EEG signals.

19. The method of claim 14, wherein computing the statistical models comprise computing a plurality of statistical models based on a plurality of different classification or regression algorithms, each of the plurality of statistical models is computed based on a first time interval portion of the at least one wet EEG and the at least one dry EEG signals, and selecting the statistical model from the plurality of statistical models according to a probability of accurate prediction within the tolerance requirement using the remaining time interval portion of the at least one wet EEG and the at least one dry EEG signals.

20. The method of claim 14, wherein the computing of the statistical model further comprises computing a feature space using power measured at each of a plurality of frequency bands compute for each of a plurality of dry EEG signals measured over a current and potentially previous time windows.

21. The method of claim 14, further comprising processing the at least one wet EEG and the at least one dry EEG signal to identify a plurality of frequency bands, and training the statistical model to simulate the at least one wet EEG signal for each of the plurality of frequency bands, wherein the plurality of frequency bands are selected from the group consisting of: theta (4-7 hertz (Hz)), alpha1 (8-10 Hz), alpha2 (11-13 Hz), beta1 (12-15 Hz), and beta2 (16-25 Hz).

22. The method of claim 14, wherein the statistical model is trained based on linear discriminant analysis (LDA) methods.

\* \* \* \* \*